US008969043B2

(12) United States Patent
Schaub et al.

(10) Patent No.: US 8,969,043 B2
(45) Date of Patent: Mar. 3, 2015

(54) METHOD FOR A RATIONAL CELL CULTURING PROCESS

(75) Inventors: Jochen Schaub, Biberach an der Riss (DE); Torsten Schulz, Hayward, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 220 days.

(21) Appl. No.: 13/321,877

(22) PCT Filed: May 27, 2010

(86) PCT No.: PCT/EP2010/057305
§ 371 (c)(1),
(2), (4) Date: Mar. 30, 2012

(87) PCT Pub. No.: WO2010/136515
PCT Pub. Date: Dec. 2, 2010

(65) Prior Publication Data
US 2012/0190005 A1    Jul. 26, 2012

(30) Foreign Application Priority Data

May 28, 2009  (EP) .................................... 09161407
Sep. 21, 2009  (EP) .................................... 09170830

(51) Int. Cl.
*C12P 21/00*    (2006.01)
*G01N 33/50*    (2006.01)
*G01N 33/92*    (2006.01)

(52) U.S. Cl.
CPC ............ *G01N 33/5005* (2013.01); *G01N 33/92* (2013.01)
USPC ..................................................... 435/70.1

(58) Field of Classification Search
None
See application file for complete search history.

(56) References Cited

FOREIGN PATENT DOCUMENTS

WO    2005047490 A2    5/2005
WO    2008033517 A2    3/2008

OTHER PUBLICATIONS

Altamirano et al., Electronic Journal of Biotechnology, vol. 9, No. 1, pp. 61-67, 2006, available online at www.ejbiotechnology.info/content/vol9/issue1/full/8/.*
Nissom et al., Molecular Biotechnology, vol. 34, pp. 125-139, 2006.*
Yee et al., (Biotechnology and Bioengineering, vol. 101, No. 6, pp. 1359-1365, 2008.*
Altamirano C. et al: "Strategies for fed-batch cultivation of t-PA producing CHO cells: substitution of glucose and glutamine and rational design of culture medium" Journal of Biotechnology, vol. 110, No. 2, May 27, 2004, pp. 171-179.
International Search Report for PCT/EP2010/057305 mailed Aug. 19, 2010.
Pascoe Deborah et al: "Proteome analysis of anti-body-producing CHO cell lines with different metabolic profiles" Biotechnology and Bioengineering. vol. 98, No. 2, Oct. 2007, pp. 391-410.
Schaub Jochen et al: "CHO Gene Expression Profiling in Biopharmaceutical Process Analysis and Design" Biotechnology and Bioengineering, vol. 105, No. 2, Feb. 2010, pp. 431-438.
Yee Joon Chong et al: "Comparative Transcriptome Analysis to Unveil Genes Affecting Recombinant Protein Productivity in Mammalian Cells" Biotechnology and Bioengineering, vol. 102, No. 1, Jan. 2009, pp. 246-263.

* cited by examiner

*Primary Examiner* — Allison Fox
*Assistant Examiner* — Yvonne Pyla
(74) *Attorney, Agent, or Firm* — Michael P. Morris; Edouard G. Lebel; Edward S. Lazer (57) ABSTRACT

Biopharmaceutical process development with recombinant protein producing mammalian cells has realized a tremendous increase in both productivity and product yields in the past years. These achievements can be mainly attributed to the advancements in cell line development, media, and process optimization. Only recently, genome-scale technologies enable a system-level analysis to elucidate the complex biomolecular basis of protein production in mammalian cells promising an increased process understanding and the deduction of knowledge-based approaches for further process optimization. The present invention describes a method for a rational cell culturing process using such a knowledge-based approach.

3 Claims, 7 Drawing Sheets

| GENE | FC HIGH TITER PROCESS | | | | | | FC LOW TITER PROCESS | | | | | | DESCRIPTION |
|---|---|---|---|---|---|---|---|---|---|---|---|---|---|
| | d2/d0 | d4/d0 | d6/d0 | d8/d0 | d9/d0 | d11/d0 | d14/d0 | d2/d0 | d4/d0 | d6/d0 | d8/d0 | d9/d0 | d11/d0 | |
| CARBOHYDRATE AND AMINO ACID METABOLISM | | | | | | | | | | | | | | |
| GALK1 | -1.3 | -1.8 | -1.9 | -2.1 | -2.4 | -2.9 | -3.2 | -1.1 | -1.2 | -1.6 | -2.1 | -2.7 | -4.0 | galactokinase 1 |
| MAOA | -1.0 | 1.0 | 1.3 | 3.0 | 2.6 | 3.4 | 2.9 | 1.1 | 1.0 | 1.2 | 1.3 | -1.0 | 1.4 | monoamine oxidase A |
| MAT2A | -2.8 | -2.6 | -2.7 | -2.7 | -2.6 | -2.3 | -2.5 | -1.0 | 1.0 | -2.7 | -2.2 | -2.4 | -1.5 | methionine adenosyltransferase II, alpha |
| PGK1 | -1.6 | -1.9 | -2.0 | -2.2 | -2.6 | -3.3 | -3.6 | -1.4 | -1.4 | -1.8 | 1.0 | 1.1 | -1.1 | phosphoglycerate kinase 1 |
| PGM2 | -3.1 | -2.4 | -2.1 | -1.8 | -1.6 | -1.2 | -1.1 | -2.6 | -2.1 | -3.6 | 1.2 | 1.6 | 2.0 | phosphoglucomutase 2 |
| UGP2 | -1.2 | 1.5 | 1.3 | 1.7 | 2.0 | 2.6 | 3.1 | -1.6 | -1.4 | -1.4 | 1.9 | -1.1 | 1.1 | UDP-glucose pyrophosphorylase 2 |
| ENERGY METABOLISM | | | | | | | | | | | | | | |
| ATP6V0D1 | -1.0 | 1.6 | 1.6 | 1.9 | 2.1 | 2.8 | 3.0 | -1.3 | -1.3 | 1.2 | 1.3 | 1.6 | 1.2 | ATPase, H+ transporting, lysosomal V0 subunit D1 |
| ATP6V0E | -1.1 | 1.3 | 1.6 | 1.9 | 2.1 | 2.1 | 2.3 | -1.2 | 1.0 | -2.6 | -1.0 | -1.3 | -1.5 | ATPase, H+ transporting, lysosomal V0 subunit D1 |
| CHST11 | 1.2 | 1.9 | 1.8 | 2.4 | 2.5 | 2.5 | 2.2 | 1.0 | 1.2 | 1.5 | 1.9 | 2.0 | 1.9 | carbohydrate sulfotransferase 11 |
| LIPID METABOLISM | | | | | | | | | | | | | | |
| ACAA2 | -1.0 | 1.6 | 1.8 | 2.2 | 2.3 | 2.2 | 2.1 | -1.4 | -1.2 | -1.8 | -2.1 | -2.6 | -3.9 | acetyl-CoA acyltransferase 2 (mitochondrial) |
| ACADM | 2.1 | 2.0 | 1.6 | 2.2 | 2.2 | 2.4 | 2.8 | -1.0 | -1.1 | -1.3 | 1.2 | 1.1 | -1.2 | acetyl-Coenzyme A dehydrogenase, medium chain |
| ACSL1 | -1.5 | 1.6 | 1.3 | 2.0 | 2.1 | 2.7 | 3.2 | -1.9 | -1.5 | -1.6 | -2.2 | -2.4 | -1.5 | acyl-CoA synthetase long-chain family member 1 |
| CHPT1 | 1.6 | 1.9 | 2.3 | 3.9 | 4.7 | 6.4 | 5.5 | -1.2 | -1.0 | 1.0 | 1.2 | 1.1 | -1.7 | choline phosphotransferase 1 |
| DHCR24 | 1.6 | 2.2 | 2.0 | 2.4 | 2.2 | 2.2 | 2.3 | 1.1 | 1.2 | -1.1 | -1.1 | 1.4 | 1.4 | 24-dehydrocholesterol reductase |
| HMGCR | -1.6 | -1.2 | -1.9 | -1.8 | -2.2 | -2.8 | -2.8 | 1.2 | 1.2 | -2.7 | -1.1 | -1.3 | -1.3 | 3-hydroxy-3-methylglutaryl-Coenzyme A reductase |
| LIP1 | -1.3 | 1.3 | 2.0 | 3.8 | 4.7 | 6.2 | 6.8 | -1.2 | -1.2 | -2.5 | 1.2 | -1.3 | -1.2 | lysosomal acid lipase 1 |
| MVK | 1.3 | 2.5 | 1.3 | 1.4 | 1.3 | 1.1 | 1.2 | -1.5 | -1.2 | -1.3 | 1.4 | 1.3 | -1.1 | mevalonate kinase |
| PECI | 1.2 | 1.8 | 1.9 | 2.6 | 2.9 | 3.4 | 3.4 | 1.2 | -1.2 | -2.8 | -1.6 | -2.7 | -3.3 | peroxisomal delta3, delta2-enoyl-CoA isomerase |
| PPAP2A | 1.7 | 1.7 | 2.4 | 3.7 | 3.8 | 3.2 | 2.9 | -1.2 | -1.2 | -1.8 | -1.8 | -2.5 | -5.4 | phosphatidic acid phosphatase 2a |
| SGPL1 | -2.1 | -1.7 | -1.5 | -1.3 | -1.2 | -1.0 | 1.0 | -1.1 | 1.1 | -1.6 | 1.4 | -1.2 | 1.1 | sphingosine phosphate lyase 1 |
| SMPD1 | -1.0 | 1.3 | 1.5 | 2.1 | 2.2 | 2.7 | 3.5 | -2.0 | -1.2 | -1.8 | 1.1 | 1.3 | 1.0 | sphingomyelin phosphodiesterase 1, acid lysosomal |
| TMEM23 | 1.2 | 1.6 | 1.8 | 2.7 | 2.8 | 2.8 | 2.5 | -1.3 | 1.0 | 1.5 | 1.7 | 2.1 | 2.3 | transmembrane protein 23 |
| NUCLEOTIDE METABOLISM | | | | | | | | | | | | | | |
| DHODH | 2.1 | 1.3 | 1.3 | 1.1 | 1.0 | -1.3 | -1.3 | 1.4 | 1.4 | -1.0 | -1.3 | -1.4 | -1.3 | dihydroorotate dehydrogenase |
| POLA1 | -1.0 | -1.5 | -1.5 | -1.9 | -2.4 | -2.3 | -1.9 | 1.1 | 1.0 | -1.1 | -1.1 | -1.4 | -1.5 | polymerase (DNA directed), alpha 1 |
| POLA2 | 2.0 | -1.0 | 1.1 | -1.2 | -1.1 | -1.2 | -1.5 | 1.1 | 1.0 | -1.8 | -2.5 | -2.2 | -2.2 | polymerase (DNA directed), alpha 2 |
| POLD1 | 1.6 | -1.6 | -1.5 | -2.1 | -2.9 | -4.1 | -2.8 | 1.1 | 1.1 | -1.7 | -2.9 | -3.4 | -2.8 | DNA polymerase delta catalytic subunit |
| PRIM1 | 1.5 | -1.8 | -1.2 | -2.1 | -2.7 | -3.1 | -2.6 | 1.1 | 1.0 | -1.6 | -2.4 | -3.2 | -3.8 | DNA primase, p49 subunit |
| RRM1 | 1.4 | -1.8 | -1.3 | -3.3 | -4.6 | -7.4 | -6.0 | -1.0 | 1.0 | -3.2 | -3.9 | -3.7 | -5.9 | ribonucleotide reductase M1 |
| TK1 | 1.5 | -1.0 | 1.3 | -1.9 | -2.9 | -4.8 | -4.6 | -1.1 | 1.0 | -2.2 | -2.8 | -3.2 | -3.9 | thymidine kinase 1 |

FIG. 3B

| GENE | FC CONTROL | | | | FC + LIPIDS | | | | FC HIGH TITER PROCESS | | | | | | | FC LOW TITER PROCESS | | | | | | DESCRIPTION |
|---|---|---|---|---|---|---|---|---|---|---|---|---|---|---|---|---|---|---|---|---|---|---|
| | d4/d0 | d6/d0 | d8/d0 | d12/d0 | d4/d0 | d6/d0 | d8/d0 | d12/d0 | d2/d0 | d4/d0 | d6/d0 | d8/d0 | d9/d0 | d11/d0 | d14/d0 | d2/d0 | d4/d0 | d6/d0 | d8/d0 | d9/d0 | d11/d0 | |
| ACAA1B | 1.2 | 1.5 | 1.6 | 1.3 | 1.5 | 1.9 | 2.1 | 1.7 | 1.2 | 1.5 | 1.8 | 1.9 | 1.9 | 2.1 | 2.0 | -1.2 | -1.1 | -1.8 | -1.2 | -1.2 | -1.8 | acetyl-Coenzyme A acyltranferase |
| ACAA2 | -1.3 | -1.0 | 1.0 | 1.2 | -1.3 | -1.1 | 1.2 | 1.1 | -1.0 | 1.6 | 1.8 | 2.2 | 2.3 | 2.2 | 2.1 | -1.4 | -1.2 | -1.8 | -2.1 | -2.6 | -3.9 | acetyl-CoA acyltransferase 2 (mitochondrial) |
| ACSL1 | 1.1 | 1.0 | 1.3 | 1.6 | -1.5 | -1.1 | 1.0 | 1.7 | -1.5 | 1.6 | 1.3 | 2.0 | 2.1 | 2.7 | 3.2 | -1.9 | -1.5 | -1.6 | 1.1 | -1.2 | -1.7 | acyl-CoA synthetase long chain family member 1 |
| ADFP | -1.5 | -1.7 | -1.3 | -1.1 | -4.5 | -4.3 | -3.0 | -3.2 | -1.0 | 1.0 | 1.2 | 1.5 | 1.7 | 1.6 | 1.6 | -1.3 | -1.3 | -1.1 | -1.0 | -1.7 | 1.1 | adipose differentiation related protein |
| CPT2 | -1.0 | 1.1 | 1.1 | 1.5 | -1.0 | 1.1 | 1.2 | 1.3 | 1.3 | 1.4 | 1.4 | 1.5 | 1.4 | 1.4 | 1.2 | -1.0 | -1.1 | -1.7 | -1.4 | -1.9 | -4.1 | carnitine palmitoyltransferase 2 |
| FABP4 | -1.4 | 3.4 | 5.7 | 11.3 | -1.8 | 1.7 | 4.4 | 13.1 | -2.3 | 2.7 | 5.4 | 17.8 | 23.5 | 33.7 | 29.6 | -2.8 | -1.3 | -1.7 | -1.8 | -2.2 | -2.4 | fatty acid binding protein 4 |
| HMGCR | -1.1 | -1.6 | -1.5 | -1.3 | -2.4 | -2.7 | -2.9 | -2.2 | -1.6 | -1.2 | -1.9 | -1.8 | -2.2 | -2.8 | -2.8 | 1.1 | -1.2 | -2.5 | 1.2 | -1.3 | -1.2 | 3-hydroxy-3-methylglutaryl-Coenzyme A reductase |
| PECI | 1.0 | 1.5 | 1.5 | 1.6 | 1.1 | 1.6 | 1.8 | 2.0 | 1.2 | 1.8 | 1.9 | 2.6 | 2.9 | 3.4 | 3.4 | -1.2 | -1.2 | -1.7 | -1.8 | -2.5 | -5.4 | peroxisomal delta3, delta2-enoyl-CoA isomerase |
| PPAP2B | 1.0 | 1.6 | 1.9 | 1.6 | -2.0 | -1.5 | -1.5 | -1.6 | -1.2 | 1.3 | 1.9 | 1.6 | 1.8 | 1.7 | 1.7 | -1.3 | 1.1 | 2.1 | 1.1 | 1.3 | -1.7 | phosphatidic acid phosphate type 2B |

METHOD FOR A RATIONAL CELL CULTURING PROCESS

BACKGROUND OF THE INVENTION

1. Technical Field

Biopharmaceutical process development with recombinant protein producing mammalian cells has realized a tremendous increase in both productivity and product yields in the past years. These achievements can be mainly attributed to the advancements in cell line development, media, and process optimization. Only recently, genome-scale technologies enable a system-level analysis to elucidate the complex biomolecular basis of protein production in mammalian cells promising an increased process understanding and the deduction of knowledge-based approaches for further process optimization.

2. Background

Biopharmaceutical process development faces the challenge to develop high titer processes for the production of clinical-grade material for toxicology studies obeying tight project timelines. Within this time-frame the design of the expression system, the generation and selection of stable high-producer cell clones (mainly CHO cells, hybridomas, BHK, and NS0 cells), and the design of scalable bioprocesses including media optimization and process control need to be addressed to maximize cell specific productivity and product yields. In recent years, we have seen enormous product titer increases in recombinant mammalian cell culture with, for example, product concentrations clearly above 5 g/L for immunoglobulins produced in CHO cells today. Achievements in molecular and cell biology including cell line engineering, in media design, and in process control strategies (e.g. by nutrient feeding) paved the way to this progress.

Though aiming at a more macroscopic bioprocess analysis, e.g. by application of online spectroscopy, knowledge-based continuous process improvements based on comprehensive process data analysis is also brought forward by the FDA as manifested in its Process Analytical Technology (PAT) initiative that motivates continuous and innovative (bio)pharmaceutical process development.

From a process science perspective there exists the challenge that further process improvement will require a more detailed knowledge of the (intra)cellular production system itself, that is an increased understanding of the physiological phenotype as observed in a given cultivation system (e.g. microtiter plate, shake flask, bench or production-scale bioreactors). At this, the main challenge is given by the fact that the flow of biological information and material flux in a cell occurs at many different levels and follows complex control mechanisms. The advancement of large-scale technologies, such as transcriptomics, proteomics or metabolomics, can provide plenty of data on the state of a biological system. However, the genetic and physiological properties that make a certain cell to a high producer cell are complex and not fully understood yet (Seth G, Charaniya S, Wlaschin K F, Hu W S. In pursuit of a super producer-alternative paths to high producing recombinant mammalian cells. Curr Opin Biotechnol 2007; 18:p 557-564).

Essentially, the application to industrial process development requires that the data from these genome-scale technologies can be transformed into information amenable to bioprocess design. Gene expression profiling allows large-scale transcript data generation on well established and robust experimental platforms. However, important physiological information, e.g. on post-translational modifications, enzyme activities or metabolic fluxes, can not be elucidated by this technology. Moreover, industrially relevant mammalian cell lines such as Chinese hamster ovary cells (CHO) still lack genome sequence information.

SUMMARY OF THE INVENTION

In the present invention, gene expression profiling was performed as a proof of principle experiment in an IgG producing CHO cell line cultivated in industrial fed batch process formats using a CHO specific Affymetrix microarray (Wlaschin K F, Nissom P M, Gatti M L, Ong P F, Arleen S, Tan K S, Rink A, Cham B, Wong K, Yap M, Hu W S. EST sequencing for gene discovery in Chinese hamster ovary cells. Biotechnol Bioeng 2005; 91:p 592-606; Yee J C, Wlaschin K F, Chuah S H, Nissom P M, Hu W S. Quality assessment of cross-species hybridization of CHO transcriptome on a mouse DNA oligo microarray. Biotechnol Bioeng 2008; 101:p 1359-1365) to assess the potential use of this technology in biopharmaceutical process development. Specifically and exemplary, we investigated the number and extent of gene deregulation during the time course of a representative high titer and a low titer fed batch process applying two different nutritional regimes. We assigned metabolic networks and biological functions to identified differentially expressed genes, and, using the example of lipid metabolism, evaluated if gene expression data combined with a pathway-oriented data analysis can also be used to optimize media composition of a standard process format in a rational way. Surprisingly and for the first time, a cell culturing process is designed based on intracellular data, preferably based on gene expression data. In state-of-the-art cell culturing process design relevant media compounds and/or (by-)products from cell metabolism are determined (i) only in the (extracellular) supernatant and (ii) the number of measured compounds is limited (usually less than about 30 compounds). In contrast, the present invention uses intracellular information from gene expression data, preferably on metabolic pathways, and large-scale datasets (about 100 up to about 2000 data from gene expression analysis).

The present invention solves the problem of further process improvement based on knowledge of the (intra)cellular production system itself by providing a method for a rational cell culturing process comprising:

a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways according to the following criteria:
  i. signal intensity values ≥40, preferably ≥80
  ii. p-value ≤0.1, preferably ≤0.05
  iii. log 2 fold change (FC) of |FC|≥1.5, preferably ≥2.0,
  iv. FC criteria (iii) to be satisfied for at least one time point of the cultivation time, preferably for cultivation day ≤8,
g) identifying at least one deregulated component of the lipid metabolism,
h) cultivating said organism of step a) according to a process C, which is different from process A and process B, whereby said cultivation process C is adjusted by adding, modifying or omitting at least one component of step g).

The present invention exemplary describes the use of gene expression profiling for the analysis of a low titer (process A) and high titer (process B) fed batch process using the same IgG producing CHO cell. We find that gene expression (i) significantly differs in high titer versus low titer process conditions, (ii) changes over the time course of the fed batch processes, and that (iii) both metabolic pathways and biological functions such as cellular growth or cell death are affected. Furthermore, detailed analysis of metabolism in a standard process format (process C) reveals the potential use of transcriptomics for rational media design as is shown for the case of lipid metabolism where the product titer can be increased by about 20% based on a lipid modified basal medium.

The results demonstrate that gene expression profiling is an important tool for mammalian biopharmaceutical process analysis and optimization.

Surprisingly and for the first time, the present invention describes a cell culturing method for cultivating an organism according to a process C, which is different from a previously measured process A and a previously measured process B, whereby said cultivation process C is adjusted by adding, modifying or omitting at least one component determined by identifying biological functions and metabolic pathways which relate to the two different processes A and B and their respective performance levels. It is quite surprising that the results of the comparison of a process A and a process B can be successfully transferred to a process C for the purpose of cell culturing process improvement.

DESCRIPTION OF THE FIGURES

FIG. 1. Time course data in high titer (HT) and low titer (LT) CHO fed batch cultivations. A) Specific growth rate (g), viability, and normalized viable cell concentration (VCC, normalization to maximal VCC of HT process), B) Recombinant IgG product concentration (titer) and specific productivity (qp). Only positive (=formation) rates are depicted. Sampling times for RNA extraction were d=0, 2, 4, 6, 8, 9, 11, 14 (only HT).

FIG. 2. A) Number of deregulated genes (p-value ≤0.05) in HT and LT processes until day 6 of cultivation, and in HT process until day 14 of cultivation as a function of applied fold change (FC) criteria.

B) Corresponding functional classification of deregulated genes. Genes were considered to be differentially expressed when the FC of at least one sampling time was |FC≥2|. Note that single genes can be involved in multiple biological functions (e.g. cell death and apoptosis).

FIG. 2 C. Differentially expressed genes associated with cellular metabolism (criteria for differential gene expression: average signal intensities of HT and LT process ≥80, p-value ≤0.05, |FC≥2| for at least one sampling time d≤9). In the heat map bold numbers denote up-regulated (positive FC values) and non-bold, normal print numbers down-regulated (negative FC values) genes. Note that mapping of genes to metabolic pathways is not always unique.

FIG. 3. A) Recombinant IgG product concentration (titer) and normalized VCC (normalization to maximal VCC of control process) of control and lipid modified fed batch processes for selected times. Sampling times for RNA extraction were d=0, 4, 6, 8, 12. B) Differentially expressed genes associated with lipid metabolism for control (first column) and lipid modified process (second column). For better comparison, also gene expression data for the HT (third column) and LT (fourth column) processes are shown. Genes ACAA1B, ADFP, CPT2, and PPAP2B exhibited a |FC≤21 for d≤9 in the HT process. Bold numbers denote up-regulated (positive FC values) and non-bold, normal print numbers down-regulated (negative FC values) genes.

DETAILED DESCRIPTION OF THE INVENTION

Figure 1A:
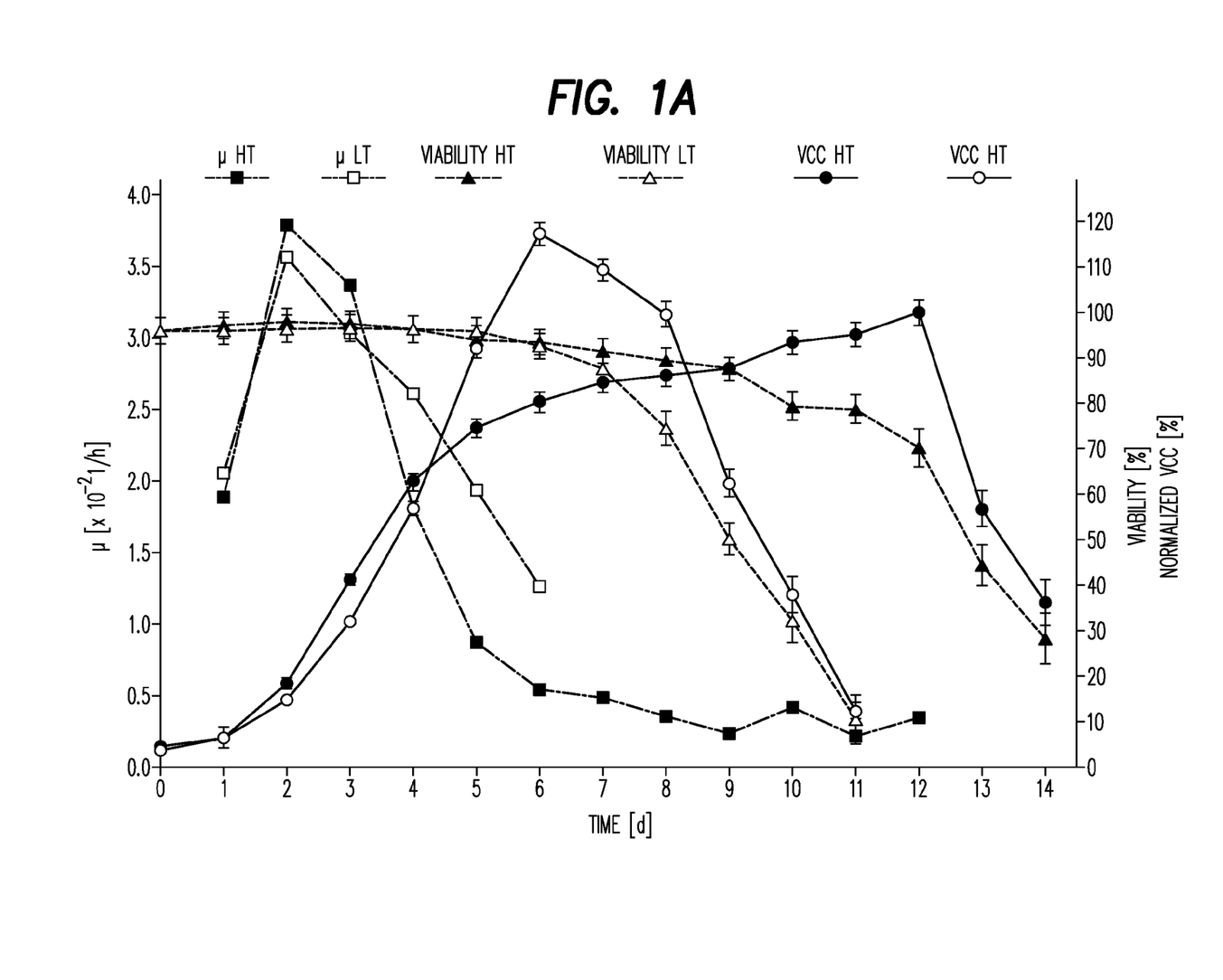
Figure 1B:
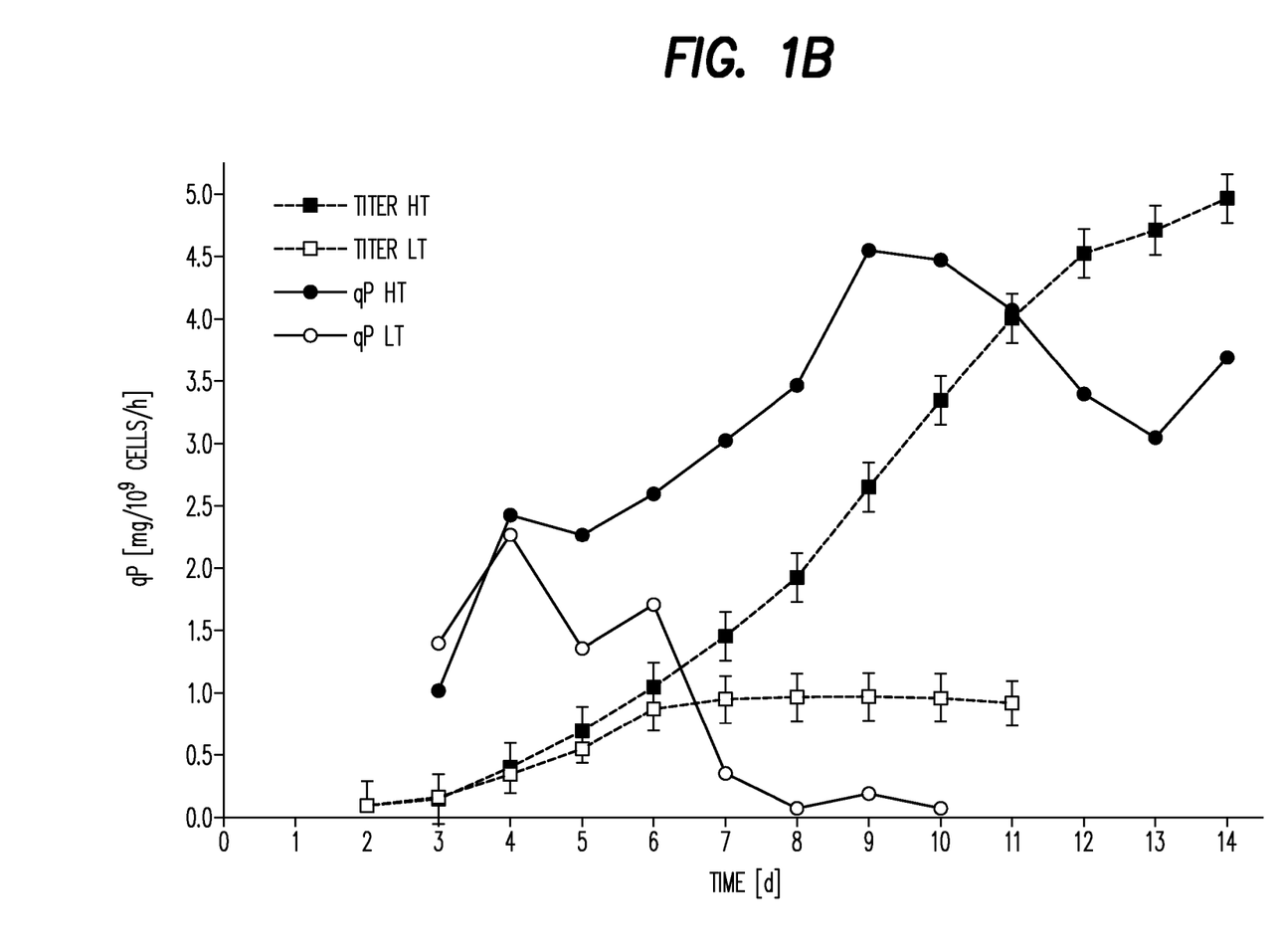

High titer (process A) and low titer (process B) CHO fed batch cultivations display significant differences in terms of growth and product formation over cultivation time (FIGS. 1A and 1B). Whereas observed differences are minor until d=4 of the two fermentation runs, the LT process is characterized by a sharp increase in viable cell concentration (VCC) up to 117% of the HT process but only a small increase in product titer until d=6, and a steep decline in VCC associated with a recombinant product concentration of about 1 g/L at d=7 that remains constant at this level until fermentation end at d=11. In contrast, in the HT process a moderate but continuous increase of VCC can be observed until d=12, product concentration increases throughout the fermentation run up to a final product titer of 5.0 g/L (d=14) though at a lower rate from d=12 to 14 when VCC decreases. Having almost the same specific growth rates at fermentation start, the LT process exhibits higher growth rates only at d=4 to 6 whereas the HT process shows positive growth rates beyond d=6 (FIG. 1A). Specific rates of product formation are similar at d=3 and 4, however they increase over fermentation time with highest values at d=9 and 10 in the HT process and decreased in the LT process (FIG. 1B).

Gene expression profiling has the potential to provide large amounts of intracellular data, thereby complementing extracellular concentration and rate (e.g. substrate uptake, product excretion) data that are routinely determined to evaluate bioprocess performance. However, transcript data cannot discern intracellular changes in the expressed phenotype on the reaction level, i.e. amounts of (active) enzymes, metabolite levels, and intracellular reaction rates. Also, the number of differentially expressed genes and the extent of gene expression in mammalian cell culture typically is rather moderate as was shown, for example, in IgG producing mouse-mouse hybridoma continuous cell culture upon metabolic shift (123 deregulated sequences by MAK cDNA microarray containing 4972 genes and 5203 ESTs, FC>1.4 cutoff, p≤0.1, max FC=3.3) (Korke R, Gatti M L, Lau A L, Lim J W, Seow T K, Chung M C, Hu W S. Large scale gene expression profiling of metabolic shift of mammalian cells in culture. J Biotechnol 2004; 107:p 1-17). In IgG producing CHO cells exposed to butyrate 122 deregulated genes (about 5% of the gene probes) were identified (CHO cDNA microarray with 2602 unique gene probes, FC>1.4 cutoff, p<0.05) (De Leon G M, Wlaschin K F, Nissom P M, Yap M, Hu W S. Comparative transcriptional analysis of mouse hybridoma and recombinant Chinese hamster ovary cells undergoing butyrate treatment. J Biosci Bioeng 2007; 103:p 82-91), similarly Yee et al. observed a total of 742 deregulated genes (about 11% of the gene probes, CHO cDNA microarray with 6822 unique gene probes, FC>1.4 cutoff, p<0.05), however only 10 genes had a FC>2 (Yee J C, De Leon G M, Philp R J, Yap M, Hu W S. Genomic and proteomic exploration of CHO and hybridoma cells under sodium butyrate treatment. Biotechnol Bioeng 2008; 99:p 1186-1204). 237 deregulated genes (<4% of the gene probes) were found when cultivation temperature was changed from 37° C. to 33° C. (CHO cDNA microarray with 6822 unique gene probes, FC≥1.4 cutoff, p<0.05) (Yee J C, Gerdtzen Z P, Hu W S. Comparative transcriptome analysis to unveil genes affecting recombinant protein productivity in mammalian cells. Biotechnol Bioeng 2009; 102:p 246-263).

Figure 2A:
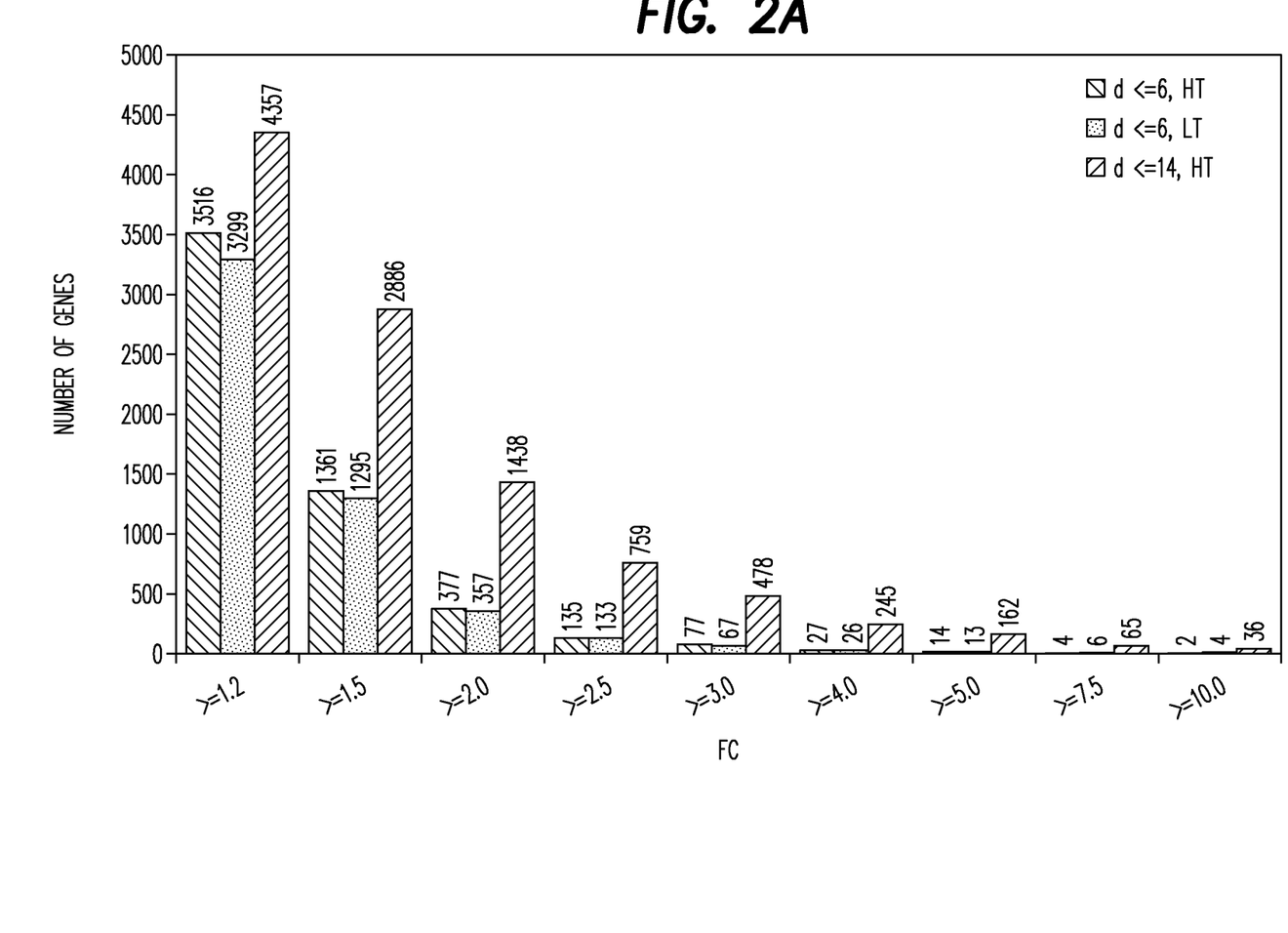
Figure 2B:
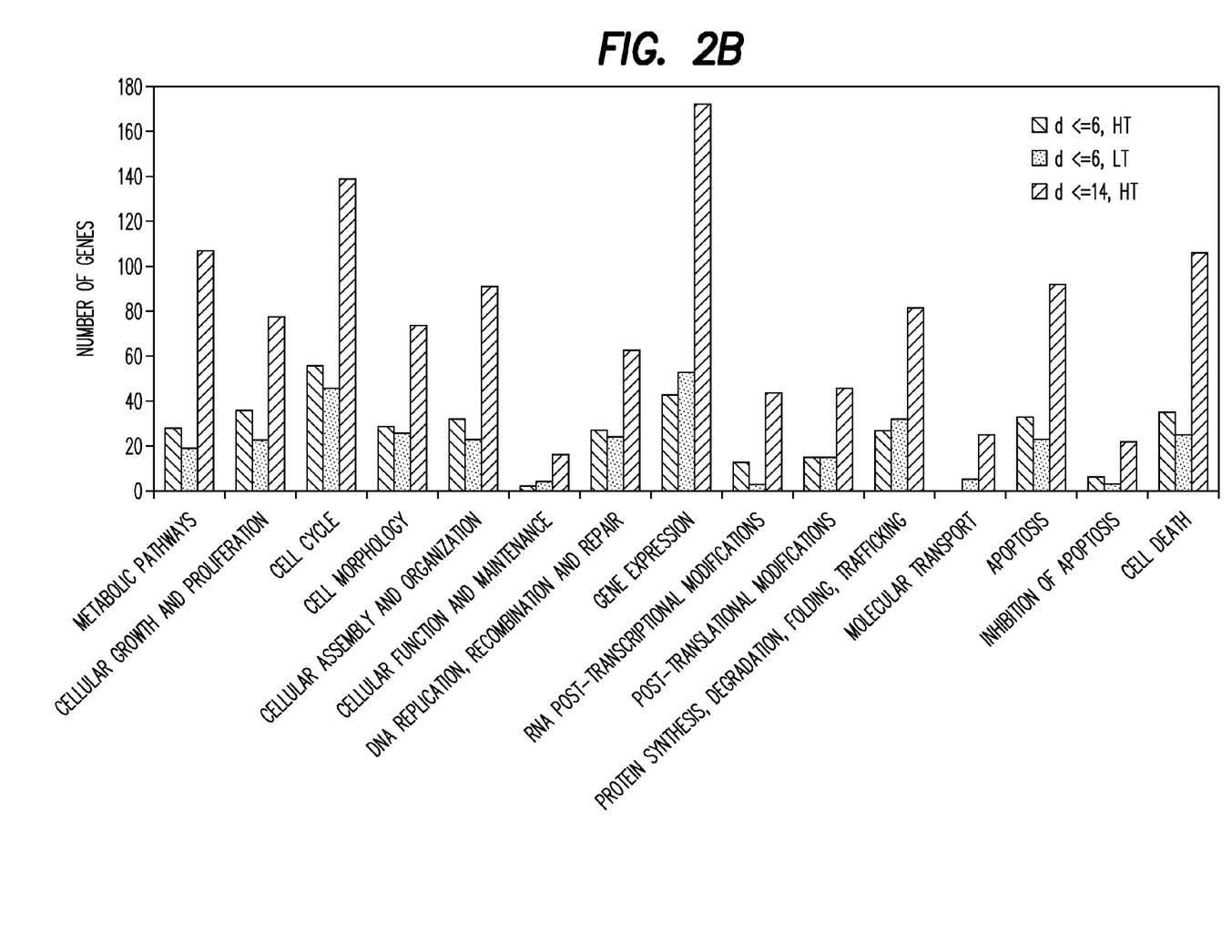

As shown in FIG. 2 A, applying a |FC≥2| cutoff, the number of identified deregulated genes in the HT process is 377 (about 5% of the unique sequences) for d≤6 (the time phase where both HT and LT processes is characterized by increasing VCC, see FIG. 1A), respectively 357 in the LT process. If all sampling times until d=14 are included, the number of deregulated genes considerably increases from 377 to 1438 as shown for the HT process. FIG. 2 B gives a detailed overview to what extent these genes are distributed among relevant biological functions and metabolic pathways. In absolute numbers, the functional classes cell cycle [56 deregulated genes], gene expression [43], cellular growth and proliferation [36], cell death [35], apoptosis [33], cellular assembly and organization [32], cell morphology [29], and metabolic pathways [28] are mostly affected for d≤6 in the HT process. The largest differences between HT and LT for d≤6 are observed for cellular growth and proliferation [13 deregulated genes], cell death, apoptosis, RNA post-transcriptional modifications, gene expression, and cell cycle [each 10], and metabolic pathways [9]. In total gene expression [172 deregulated genes], cell cycle [139], metabolic pathways [107], cell death [106], apoptosis [92], cellular assembly and organization [91], and, interestingly, protein synthesis, degradation, folding, and trafficking [82] essentially accounted for the large number of deregulated genes in the HT process for d≤14 (FIG. 2 B). For application of transcriptomics in bioprocess analysis and optimization, namely media design, insight into cellular metabolism is of particular importance. FIG. 2 C summarizes genes from important metabolic pathways (carbohydrate and amino acid, energy, lipid, and nucleotide metabolism) with focus on lipid metabolism that are found to be significantly up- or down-regulated in the HT process. A rather conservative |FC≥2| cutoff is applied (compare FIG. 2 A) that has to be exceeded for d≤9 of the HT process (viability of about 90% or higher). Altogether, from the 10118 probe sets, 6769 sequences have intensity values above 80, 4711 have a p-value ≤0.05, and 58 sequences (without doubles) can be mapped to metabolic pathways.

Remarkably, genes from energy and lipid metabolism are significantly (and increasingly) up-regulated during the time course of the HT process compared to the LT process. Since the up-regulation of several genes involved in lipid metabolism can be indicative for a potential limitation in the precursor supply, the chemically defined lipid concentration in the basal medium is increased threefold in a second fermentation experiment applying a standard process format (process C). Lipids serve as structural components, e.g. in membranes of cell organelles where they play an important role in the synthesis and the transport of recombinant proteins, they also serve as potential energy sources and can be readily metabolized if extracellularly supplied with the cell culture medium (e.g. as fatty acids, lipid esters, phospholipids or cholesterol). In this standard process format a lower product titer of about 3.2 g/L (vs. 5.0 g/L) at d=14 is achieved (FIG. 3A) compared to the HT process (FIG. 1 A).

Figure 3A:
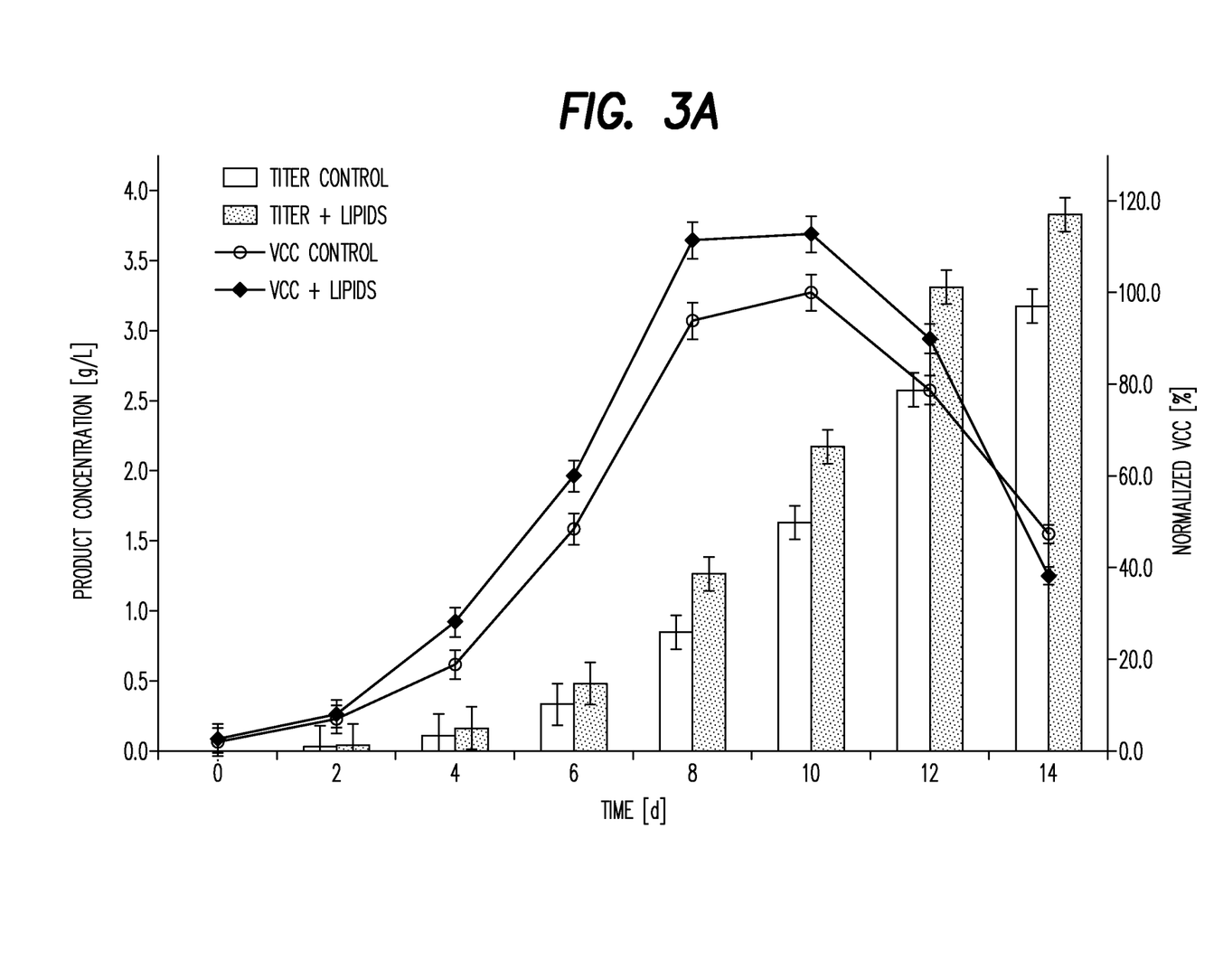

Surprisingly, by use of the modified basal media with an increased lipid concentration, the final product titer can be increased by approximately 20% from 3.18±0.10 g/L to 3.83±0.12 g/L at d=14 compared to the control (FIG. 3 A), the relative increase at d=12 of about 28% is even larger due to the higher VCC.

FIG. 3 B shows gene expression profiles of several lipid metabolism genes. Genes ACAA2, ACSL1, CPT2, and PECI are up-regulated in the HT (titer 5 g/L) and down-regulated in the LT process (titer 1 g/L), their expression values in the control (titer 3.2 g/L) and in the lipid modified standard process (titer 3.8 g/L) are somewhere in-between not allowing a distinction between those two process conditions. Only ACSL1 is found to be slightly down-regulated at d=4 (lipid modified medium). Its gene product catalyzes the first step in fatty acid β-oxidation in an ATP dependent reaction (EC 6.2.1.3), and thereby plays a key role in fatty acid metabolism. Whereas ACAA2 (EC 2.3.1.16) acts in both mitochondrial fatty acid elongation and fatty acid metabolism, genes CPT2 (EC 2.3.1.21) and PECI (EC 5.3.3.8) are involved in fatty acid metabolism. Expression of ACAA1B (EC 2.3.1.16, fatty acid metabolism) exhibit only subtle differences between control and lipid modified process and is similar to HT. ADFP playing a role in long-chain fatty acid transport and sequestering of lipids in different cellular components is significantly down-regulated in the lipid modified process in comparison with the control experiment and in contrast to the HT process. Interestingly, HMGCR that encodes a key enzyme for cholesterol synthesis (3-hydroxy-3-methylglutaryl-Coenzyme A reductase, EC 1.1.1.34) has consistent trends with the HT and LT processes, and also revealed noteworthy different gene expression for the control and the lipid modified standard process where HMGCR is much more down-regulated. PPAP2B encodes phosphatidic acid phosphatase type 2B (EC 3.1.3.4) which is involved in the de novo synthesis of glycerolipids and catalyzes the last but one step in triglyceride synthesis. Its gene expression is similar for the control and the HT process but is significantly lowered when the lipid concentration in the basal media is changed indicating that the cells respond to the supplementation of lipids. Summarizing, the altered lipid media composition induced considerable transcriptional changes and, thus, allows a targeted media improvement of a standard process format (process C) based on intracellular information on the cells physiological state using a pathway-oriented approach.

Despite the fact that genome sequence information for important mammalian producer cell lines like CHO is unavailable and transcriptomics can not reflect any post-transcriptional changes (i.e. on the protein and reaction level), this technology grants access to intracellular processes in an experimentally feasible and, in particular, large-scale approach. Significantly different gene expression patterns (also with respect to process time) are found in a high titer versus low titer CHO fed batch process. Moreover, the example of lipid metabolism demonstrated that gene expression analysis of larger biological functional units can reveal potential targets for media optimization provided that a correct biological conclusion can be drawn from the transcript data. Surprisingly it is demonstrated, that the described genome-scale technologies and methods can contribute to a faster, rational, and data-driven mammalian cell culture bioprocess development.

The general embodiments "comprising" or "comprised" encompass the more specific embodiment "consisting of". Furthermore, singular and plural forms are not used in a limiting way.

Terms used in the course of this present invention have the following meaning.

The term "rational" cell culturing process describes the design of a cell culture process using a data-driven approach, preferably based on intracellular data, preferably based on gene expression data. In state-of-the-art cell culturing process design relevant media compounds and/or (by-)products from cell metabolism are determined (i) only in the (extracellular) supernatant and (ii) the number of measured compounds is limited (usually less than about 30 compounds). In contrast, this approach uses intracellular information from gene expression data, preferably on metabolic pathways, and large-scale datasets (about 100 up to about 2000 data from gene expression analysis).

The expression "comparative method suitable to distinguish between the different performance levels of said cell in process A versus process B" preferably means gene expression profiling analysis.

The term "deregulated component" means a gene that is found to be deregulated according to the above criteria. Deregulated can mean up-regulated or down-regulated in comparison to another process. For example, up-regulation of certain genes in process B compared to process A may means that some required media compounds are not (sufficiently) supplied with the medium in process B. In the case of this process B the cell up-regulates the genes associated with the production of these media compounds in comparison with process A.

Typically, such a gene encodes for an enzyme/enzyme complex which is involved in the conversion of metabolic intermediates that are either synthesized by the cell or are supplied by the cell culture medium.

The term "lipid metabolism" means all metabolic pathways involved in lipid metabolism such as fatty acid biosynthesis, biosynthesis of unsaturated fatty acids, triglyceride synthesis, cholesterol synthesis, fatty acid metabolism, fatty acid elongation (in mitochondria), fatty acid transport, glycerolipid metabolism, glycerophospholipid metabolism, sphingolipid metabolism, arachidonic acid metabolism, linoleic acid metabolism, and/or biosynthesis of steroids.

Preferred pathways are: fatty acid biosynthesis, cholesterol synthesis, fatty acid metabolism, fatty acid elongation (in mitochondria), glycerolipid metabolism, glycerophospholipid metabolism, sphingolipid metabolism, arachidonic acid metabolism, linoleic acid metabolism, biosynthesis of steroids.

List of Genes:
ACAA2 (acetyl-CoA acyltransferase 2 (mitochondrial)), ACSL1 (acyl-CoA synthetase long-chain family member 1), CHPT1 (choline phosphotransferase 1), FABP4 (fatty acid binding protein 4), GRN (granulin), HMGCR (3-hydroxy-3-methylglutaryl-Coenzyme A reductase), LIP1 (lysosomal acid lipase 1), MVK (mevalonate kinase), PECI (peroxisomal delta3, delta2-enoyl-CoA isomerase), PPAP2A (phosphatidic acid phosphatase 2a), SGPL1 (sphingosine phosphate lyase 1), SMPD1 (sphingomyelin phosphodiesterase 1, acid lysosomal), TMEM23 (transmembrane protein 23), ACADM (acetyl-Coenzyme A dehydrogenase, medium chain), VNN1 (vanin 1), GM2A (GM2 ganglioside activator protein).

The criteria for selecting components by using gene expression analysis are:
(ii) signal intensity values ≥40, preferably ≥80
(iii) a p-value ≤0.1, preferably ≤0.05
(iv) a log 2 fold change (FC) of |FC|≥1.5, preferably ≥2.0
(v) the FC criteria (iii) to be satisfied for at least one time point of the cultivation time, preferably for cultivation day ≤8

The "p-value" is calculated based on the student's t-test. For this purpose, triplicate samples are withdrawn, processed, and hybridized on a custom-made CHO specific Affymetrix microarray.

The "log 2 fold change (FC)" is calculated according to the formula $FC=2^a/2^b$ for a>b, respectively $FC=-2^b/2^a$ for b>a, where a and b are the measured intensity values determined on an Affymetrix GeneChip Scanner 3000 system. For every sampling time the fold changes (FC) were calculated relative to the control (d=0) to analyze differential gene expression over the time course of the fed batch experiments.

The term "adjusted" means any modification of the cell culture medium by identified components that result in an improved process performance.

The adjustment may be realized by adding, modifying or omitting certain media and/or feed components. The terms "adding, modifying or omitting" mean that said improved performance can be achieved by newly adding, modifying the concentrations and/or concentration ratios, or omitting said components to/from the cell culture medium.

The present invention concerns a method for a cell culturing process/a method for culturing a cell/a method for modifying a cell culturing process comprising:
a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways according to the following criteria:
  i. signal intensity values ≥40, preferably ≥80
  ii. p-value ≤0.1, preferably ≤0.05
  iii. log 2 fold change (FC) of |FC|≥1.5, preferably ≥2.0,
  iv. FC criteria (iii) to be satisfied for at least one time point of the cultivation time, preferably for cultivation day ≤8,
g) identifying at least one deregulated component,
h) cultivating said organism of step a) according to a process C, which is different from process A and process B, whereby said cultivation process C is adjusted by adding, modifying or omitting at least one component of step g).

In a preferred embodiment said component of step g) is a component from FIG. 2C or FIG. 3b.

The present invention further concerns a method for adding, modifying or omitting at least one component of a cell culturing process comprising:
a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways according to the following criteria:
  i. signal intensity values ≥40, preferably ≥80
  ii. p-value ≤0.1, preferably ≤0.05
  iii. log 2 fold change (FC) of |FC|≥1.5, preferably ≥2.0,
  iv. FC criteria (iii) to be satisfied for at least one time point of the cultivation time, preferably for cultivation day ≤8,
g) identifying at least one deregulated component, preferably of the lipid metabolism,
h) cultivating said organism of step a) according to a process C, which is different from process A and process B, whereby said cultivation process C is adjusted by adding, modifying or omitting at least one component of step g).

In a preferred embodiment said component of step g) is a component from FIG. 2C or FIG. 3b.

The present invention furthermore concerns a method for a cell culturing process/a method for culturing a cell/a method for modifying a cell culturing process comprising:
a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways,
g) identifying at least one deregulated component of the lipid metabolism,
h) cultivating said organism of step a) according to a process C, which is different from process A and process B, whereby said cultivation process C is adjusted by adding, modifying or omitting at least one component of step g).

In a preferred embodiment said component of step g) is a component from FIG. 2C or FIG. 3b.

The present invention concerns a method for a cell culturing process/a method for culturing a cell/a method for modifying a cell culturing process comprising:
a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways according to the following criteria:
  i. signal intensity values $\geq 40$, preferably $\geq 80$
  ii. p-value $\leq 0.1$, preferably $\leq 0.05$
  iii. log 2 fold change (FC) of $|FC| \geq 1.5$, preferably $\geq 2.0$,
  iv. FC criteria (iii) to be satisfied for at least one time point of the cultivation time, preferably for cultivation day $\leq 8$,
g) identifying at least one deregulated component of the lipid metabolism,
h) cultivating said organism of step a) according to a process C, which is different from process A and process B, whereby said cultivation process C is adjusted by adding, modifying or omitting at least one component of step g).

In a preferred embodiment said component of step g) is a component from FIG. 2C or FIG. 3b.

The present invention concerns a method for a rational cell culturing process comprising:
a) providing a self-replicating organism,
b) culturing said organism according to a process A,
c) culturing said organism according to a process B, which is different from process A,
d) employing a comparative method suitable to distinguish between the different performance levels of said cell in process A versus process B,
e) identifying biological functions and metabolic pathways which relate to the two different processes A and B and their respective performance levels,
f) selecting components of deregulated metabolic pathways according to the following criteria:
  i. signal intensity values $\geq 40$, preferably $\geq 80$
  ii. p-value $\leq 0.1$, preferably $\leq 0.05$
  iii. log 2 fold change (FC) of $|FC| \geq 1.5$, preferably $\geq 2.0$,
  iv. FC criteria (iii) to be satisfied for at least one time point of the cultivation time, preferably for cultivation day $\leq 8$,
g) identifying at least one deregulated component of the lipid metabolism,
h) cultivating said organism of step a) according to a process C, which is different from process A and process B, whereby said cultivation process C is adjusted by adding, modifying or omitting at least one component of step g).

In a specific embodiment the organism in step a) is a eukaryotic cell, preferably a mammalian, rodent, hamster, CHO, most preferably a CHO-DG44 cell.

In another embodiment process A is a high titer, high cell density, high viability, high productivity, low osmotic stress, or stoichiometrically fed process, preferably a high titer process.

In a further embodiment process B is a low titer, low cell density, low viability, low productivity, high osmotic stress, or not stoichiometrically fed process, preferably a low titer process.

In a preferred embodiment the comparative method of step d) is gene expression profiling analysis, In another preferred embodiment of the present invention the at least one deregulated component of the lipid metabolism is selected from a group consisting of the following genes: ACAA2 (acetyl-CoA acyltransferase 2 (mitochondrial)), ACSL1 (acyl-CoA synthetase long-chain family member 1), CHPT1 (choline phosphotransferase 1), FABP4 (fatty acid binding protein 4), GRN (granulin), HMGCR (3-hydroxy-3-methylglutaryl-Coenzyme A reductase), LIP1 (lysosomal acid lipase 1), MVK (mevalonate kinase), PECI (peroxisomal delta3, delta2-enoyl-CoA isomerase), PPAP2A (phosphatidic acid phosphatase 2a), SGPL1 (sphingosine phosphate lyase 1), SMPD1 (sphingomyelin phosphodiesterase 1, acid lysosomal), TMEM23 (transmembrane protein 23), ACADM (acetyl-Coenzyme A dehydrogenase, medium chain), VNN1 (vanin 1) and GM2A (GM2 ganglioside activator protein). Specifically preferred are PPAP2B (phosphatidic acid phosphatase type 2B), ADFP (adipose differentiation related protein), and HMGCR (3-hydroxy-3-methylglutaryl-Coenzyme A reductase).

In a specifically preferred embodiment of the present invention the deregulated component of the lipid metabolism is PPAP2B (phosphatidic acid phosphatase type 2B).

In a further preferred embodiment of the present invention the deregulated component of the lipid metabolism is ADFP (adipose differentiation related protein).

In another preferred embodiment of the present invention the deregulated component of the lipid metabolism is HMGCR (3-hydroxy-3-methylglutaryl-Coenzyme A reductase).

In a specific embodiment 2 deregulated components are selected and used to adjust process C cultivation process. In another embodiment 3, 4, 5 or more than 5 deregulated components are selected and used to adjust process C cultivation process.

In a specific preferred embodiment at least two lipid metabolism components are identified in step g). Those at least two components in step g) are preferably selected from the group consisting of: components metabolized by enzymes encoded by genes from the pathways fatty acid biosynthesis, biosynthesis of unsaturated fatty acids, triglyceride synthesis, cholesterol synthesis, fatty acid metabolism, fatty acid elongation (in mitochondria), fatty acid transport, glycerolipid metabolism, glycerophospholipid metabolism, sphingolipid metabolism, arachidonic acid metabolism, linoleic acid metabolism and biosynthesis of steroids.

Preferred pathways in step e) are: fatty acid biosynthesis, cholesterol synthesis, fatty acid metabolism, fatty acid elongation (in mitochondria), glycerolipid metabolism, glycerophospholipid metabolism, sphingolipid metabolism, arachidonic acid metabolism, linoleic acid metabolism, biosynthesis of steroids.

The selected media compounds/components of step g) are preferably cholesterol, arachidonic acid, linoleic acid, tetradecanoic acid (myristic acid), hexadecanoic acid (palmitic acid), hexadecenoic acid (palmitoleic acid), octadecanoic acid (stearic acid) or octadecenoic acid (oleic acid).

In a further embodiment the process C is a cultivation process suitable for small scale process development and large scale biopharmaceutical production.

In a preferred embodiment the organism of step a) is a production host cell comprising a gene of interest coding for a product of interest, preferably a therapeutic protein, most preferably an antibody.

In a further preferred embodiment the method according to the invention additional encompasses:
a) production/expression of a product of interest and optionally
b) purification of said product.

The present invention also relates to a method for producing a product of interest comprising
a) providing a mammalian host cell, preferably a CHO cell,
b) culturing said cell according to a process A,
c) culturing said cell according to a process B, which is different from process A,
d) employing a comparative method suitable to distinguish between the different performance levels of said cell in process A versus process B,
e) identifying biological functions and pathways which relate to the two different processes A and B and their respective performance levels,
f) selecting components of deregulated metabolic pathways according to the following criteria:
  i. signal intensity values ≥40, preferably ≥80
  ii. p-value ≤0.1, preferably ≤0.05
  iii. log 2 fold change (FC) of |FC|≥1.5, preferably ≥2.0,
  iv. FC criteria (iii) to be satisfied for at least one time point of the cultivation time, preferably for cultivation day ≤8,
g) identifying at least one deregulated component of the lipid metabolism,
h) cultivating said cell of step a) according to a process C, which is different from process A and process B, whereby said cultivation process C is adjusted by adding, modifying or omitting at least one component of step g).

Preferably, process A is a high titer cultivation process and process B is a low titer cultivation process and process C is a cultivation process suitable for small scale process development and large scale biopharmaceutical production.

In a specifically preferred embodiment of any of the methods of the present invention the deregulated component of the lipid metabolism is PPAP2B (phosphatidic acid phosphatase type 2B).

In a further preferred embodiment of any of the methods of the present invention the deregulated component of the lipid metabolism is ADFP (adipose differentiation related protein).

In another preferred embodiment of any of the methods of the present invention the deregulated component of the lipid metabolism is HMGCR (3-hydroxy-3-methylglutaryl-Coenzyme A reductase).

The invention generally described above will be more readily understood by reference to the following examples, which are hereby included merely for the purpose of illustration of certain embodiments of the present invention. The following examples are not limiting. They merely show possible embodiments of the invention. A person skilled in the art could easily adjust the conditions to apply it to other embodiments.

Materials and Methods
Cell Culture

Using the same recombinant IgG producing CHO cell line a high titer (HT) and a low titer (LT) fed batch cultivation is performed (25 L start volume) with a viable inoculation cell concentration of $3.0 \times 10^5$ cells/mL derived from the same inoculum preculture. In both processes temperature is controlled at 37° C., pH at 7.0, and dissolved oxygen concentration at 60% air saturation by adjusting stirrer speed (80 rpm at LT, 100-130 rpm at HT) and the oxygen fraction in the nitrogen/oxygen gas mixture. HT and LT fed batch processes differ with respect to applied proprietary chemically defined, serum-free basal and fed batch media compositions and supply. A second fed batch fermentation experiment in a standard process format (about 3 g/L recombinant IgG product concentration) is performed applying the same cultivation conditions to investigate the effect of altered concentrations of chemically defined lipids in the basal medium.

Concentrations of the key metabolites glucose, lactate, glutamine, glutamate and ammonium are measured on a daily basis for process monitoring and to ensure that concentrations of glucose and glutamine are not limiting.

Analytical Methods

Cell concentration and cell viability are determined by the trypan blue exclusion method using a CEDEX automated cell analyzer (Innovatis AG, Bielefeld, Germany). Concentration of recombinant IgG antibody concentration is quantified in duplicates by a Biacore C instrument (GE Healthcare Europe GmbH, Germany) that uses surface plasmone resonance detection of a antibody antigen complex. An YSI 2700 analyzer (YSI Incorp., Yellow Springs, USA) is used for quantification of glucose, lactate, glutamine, and glutamate in the fermentation supernatant, ammonium is enzymatically determined according to assay instructions (ammonia test kit, 11112732035, Roche Diagnostics GmbH, Mannheim, Germany) on a Konelab 20i (Thermo Fisher Scientific, Waltham, USA).

Sampling, RNA Extraction, Microarray Hybridization, and Data Processing

Samples for time-series gene expression profiling are taken in different process phases (FIGS. 1 and 3). Harvested cells ($2 \times 10^6$ cells) are centrifuged and the total RNA is extracted from the cell pellets using the RNeasy Kit (Qiagen GmbH, Hilden, Germany) according to manufacturer's protocol. 10 µg of the extracted biotin labeled cRNA was hybridized on a custom-made CHO specific Affymetrix microarray (Yee J C, Wlaschin K F, Chuah S H, Nissom P M, Hu W S. Quality assessment of cross-species hybridization of CHO transcriptome on a mouse DNA oligo microarray. Biotechnol Bioeng 2008; 101:p 1359-1365) containing 10 118 probe sets with 7525 unique sequences that represent a subset from a collection of 16 136 unique CHO cell and Chinese hamster transcripts obtained by comprehensive EST sequencing as described by Wlaschin et al. (Wlaschin K F, Nissom P M, Gatti M L, Ong P F, Arleen S, Tan K S, Rink A, Cham B, Wong K, Yap M, Hu W S. EST sequencing for gene discovery in Chinese hamster ovary cells. Biotechnol Bioeng 2005; 91:p 592-60; Wlaschin K F, Hu W S. A scaffold for the Chinese hamster genome. Biotechnol Bioeng 2007; 98:p 429-439). Samples are scanned in high-resolution mode and data are processed with an Affymetrix GeneChip Scanner 3000 system (Affymetrix Inc., Santa Clara, USA). For every sampling time the fold changes (FC) are calculated as log 2-transformed ratios relative to the control (d=0) to analyze differential gene expression over the time course of the fed batch experiments. Signal intensities below 80 are discarded as noise, p-values are calculated based on 4 biological replicates applying a cutoff of p≤0.05. Analysis of metabolic networks and biological functions is performed using Ingenuity Pathway Analysis (Ingenuity Systems Inc., Redwood City, USA) and the curated sequence database RefSeq for gene annotation (Pruitt K D, Tatusova T, Maglott D R. NCBI reference sequences (RefSeq): a curated non-redundant sequence database of genomes, transcripts and proteins. Nucleic Acids Res 2007; 35:p D61-D65).

REFERENCES

Seth G, Charaniya S, Wlaschin K F, Hu W S. In pursuit of a super producer-alternative paths to high producing recombinant mammalian cells. Curr Opin Biotechnol 2007; 18:p 557-564.

Wlaschin K F, Nissom P M, Gatti M L, Ong P F, Arleen S, Tan K S, Rink A, Cham B, Wong K, Yap M, Hu W S. EST sequencing for gene discovery in Chinese hamster ovary cells. Biotechnol Bioeng 2005; 91:p 592-606.

Yee J C, Wlaschin K F, Chuah S H, Nissom P M, Hu W S. Quality assessment of cross-species hybridization of CHO transcriptome on a mouse DNA oligo microarray. Biotechnol Bioeng 2008; 101:p 1359-1365.

Wlaschin K F, Hu W S. A scaffold for the Chinese hamster genome. Biotechnol Bioeng 2007; 98:p 429-439.

Pruitt K D, Tatusova T, Maglott D R. NCBI reference sequences (RefSeq): a curated non-redundant sequence database of genomes, transcripts and proteins. Nucleic Acids Res 2007; 35:p D61-D65.

Korke R, Gatti M L, Lau A L, Lim J W, Seow T K, Chung M C, Hu W S. Large scale gene expression profiling of metabolic shift of mammalian cells in culture. J Biotechnol 2004; 107:p 1-17.

De Leon G M, Wlaschin K F, Nissom P M, Yap M, Hu W S. Comparative transcriptional analysis of mouse hybridoma and recombinant Chinese hamster ovary cells undergoing butyrate treatment. J Biosci Bioeng 2007; 103:p 82-91.

Yee J C, De Leon G M, Philp R J, Yap M, Hu W S. Genomic and proteomic exploration of CHO and hybridoma cells under sodium butyrate treatment. Biotechnol Bioeng 2008; 99:p 1186-1204.

Yee J C, Gerdtzen Z P, Hu W S. Comparative transcriptome analysis to unveil genes affecting recombinant protein productivity in mammalian cells. Biotechnol Bioeng 2009; 102:p 246-263.

The invention claimed is:

1. A method for producing a product of interest comprising
a) providing a mammalian host cell,
b) culturing said cell according to a process A,
c) culturing said cell according to a process B, which is different from process A,
d) employing a comparative method suitable to distinguish between the different performance levels of said cell in process A versus process B,
e) identifying biological functions and pathways which relate to the two different processes A and B and their respective performance levels,
f) selecting genes of deregulated metabolic pathways according to the following criteria:
   i. signal intensity values ≥40,
   ii. p-value ≤0.1,
   iii. log 2 fold change (FC) of |FC|≥1.5,
   iv. FC criteria (iii) to be satisfied for at least one time point of the cultivation time, preferably for cultivation day ≤8,
g) identifying at least one deregulated gene of lipid metabolism,
h) cultivating said cell of step a) according to a process C, which is different from process A and process B, whereby said cultivation process C is adjusted by adding, modifying or omitting at least one component metabolized by an enzyme encoded by the identified gene of step g).

2. The method according to claim 1, whereby process A is a high titer cultivation process and process B is a low titer cultivation process and process C is a cultivation process suitable for small scale process development and large scale biopharmaceutical production.

3. The method according to claim 1, whereby the deregulated gene of the lipid metabolism is PPAP2B (phosphatidic acid phosphatase type 2B).

* * * * *